United States Patent [19]
Murugesan

[11] Patent Number: 5,846,985
[45] Date of Patent: Dec. 8, 1998

[54] SUBSTITUTED BIPHENYL ISOXAZOLE SULFONAMIDES

[75] Inventor: Natesan Murugesan, Princeton Junction, N.J.

[73] Assignee: Bristol-Myers Squibb Co., Princeton Junction, N.J.

[21] Appl. No.: 810,777

[22] Filed: Mar. 5, 1997

Related U.S. Application Data

[60] Provisional application No. 60/013,491, Mar. 12, 1996.
[51] Int. Cl.$^6$ .......................... A61K 31/41; C07D 271/10
[52] U.S. Cl. .......................... 514/364; 514/380; 548/143; 548/245; 548/246
[58] Field of Search ..................................... 548/245, 246, 548/143; 514/380, 364

[56] References Cited

U.S. PATENT DOCUMENTS 5,411,980  5/1995  Ashton et al. ......................... 514/384

Primary Examiner—Joseph K. McKane
Attorney, Agent, or Firm—Suzanne E. Babajko

[57] ABSTRACT

Compounds of the formula

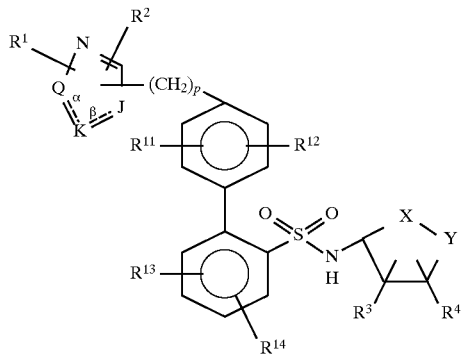

inhibit the activity of endothelin. The symbols $R^1$, $R^2$, Q, K, J, α, β, p, $R^{11}$, $R^{12}$, $R^{13}$, $R^{14}$, X, Y, $R^3$ and $R^4$ are defined herein.

28 Claims, No Drawings

SUBSTITUTED BIPHENYL ISOXAZOLE SULFONAMIDES

This application claims priority from provisional U.S. application Ser. No. 60/013,491, filed Mar. 12, 1996, incorporated herein by reference in its entirety.

FIELD OF THE INVENTION

This invention relates to endothelin antagonists useful, inter alia, for the treatment of hypertension.

BRIEF DESCRIPTION OF THE INVENTION

Compounds of the formula I:

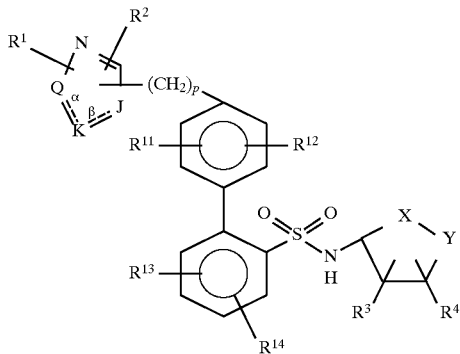

its enantiomers and diastereomers, and pharmaceutically acceptable salts thereof are endothelin receptor antagonists useful, inter alia, as antihypertensive agents. Throughout this specification, the above symbols are defined as follows:

one of X and Y is N and the other is O;

Q is N or $NR^{15}$;

J is O, S, N or $NR^{15}$;

K is C=O or CH;

the dotted line α between Q and K denotes an optional double bond when Q is N and K is CH;

the dotted line β between K and J denotes an optional double bond when K is CH and J is N;

with the proviso that said α and β double bonds may not simultaneously be present;

$R^1$ and $R^2$, when present, and $R^3$ and $R^4$, are each directly bonded to a ring carbon and are each independently (a) hydrogen;

(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;

(c) halo;

(d) hydroxyl;

(e) cyano;

(f) nitro;

(g) —C(O)H or —C(O)$R^5$;

(h) —CO$_2$H or —CO$_2R^5$;

(i) —$Z^4$—$NR^6R^7$; or (j) —$Z^4$—N($R^{10}$)—$Z^5$—$NR^8R^9$; and (k) $R^3$ and $R^4$ together may also be alkylene or alkenylene, either of which may be substituted with $Z^1$, $Z^2$ and $Z^3$, completing a 4- to 8-membered saturated, unsaturated or aromatic ring together with the carbon atoms to which they are attached;

$R^5$ is alkyl, alkenyl, alkynyl, cycloalkyl, cycloalkylalkyl, cycloalkenyl, cycloalkenylalkyl, aryl or aralkyl, any of which may be substituted with $Z^1$, $Z^2$ and $Z^3$;

$R^6$, $R^7$, $R^8$, $R^9$ and $R^{10}$ are each independently (a) hydrogen; or (b) alkyl, cycloalkyl, cycloalkylalkyl, cycloalkenylalkyl, aryl or aralkyl, any of which may be substituted with $Z^1$, $Z^2$ and $Z^3$; or $R^6$ and $R^7$ together may be alkylene or alkenylene, either of which may be substituted with $Z^1$, $Z^2$ and $Z^3$, completing a 3- to 8-membered saturated or unsaturated ring together with the nitrogen atom to which they are attached; or any two of $R^8$, $R^9$ and $R^{10}$ together are alkylene or alkenylene, either of which may be substituted with $Z^1$, $Z^2$ and $Z^3$, completing a 3- to 8-membered saturated or unsaturated ring together with the atoms to which they are attached;

$R^{11}$, $R^{12}$, $R^{13}$ and $R^{14}$ are each independently (a) hydrogen;

(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$, (c) heterocyclo, substituted heterocyclo or heterocyclooxy;

(d) halo;

(e) hydroxyl;

(f) cyano;

(g) nitro;

(h) —C(O)H or —C(O)$R^5$;

(i) —CO$_2$H or —CO$_2R^5$; (j) —SH, —S(O)n$R^5$, —S(O)m-OH, —S(O)m—O$R^5$, —O—S(O)m—O$R^5$, —O—S(O)mOH or —O—S(O)m—O$R^5$;

(k) —$Z^4$—$NR^6R^7$; or (l) —$Z^4$—N($R^{10}$)—$Z^5$—$NR^8R^9$; $Z^1$, $Z^2$ and $Z^3$ are each independently (a) hydrogen;

(b) halo;

(c) hydroxy;

(d) alkyl;

(e) alkenyl;

(f) aryl;

(g) aralkyl;

(h) alkoxy;

(i) aryloxy;

(j) aralkoxy;

(k) heterocyclo, substituted heterocyclo or heterocyclooxy;

(l) —SH, —S(O)$_n Z^6$, —S(O)$_m$—OH, —S(O)$_m$—O$Z^6$, —O—S(O)m—$Z^6$, —O—S(O)$_m$OH or —O—S(O)$_m$—O$Z^6$;

(m) oxo;

(n) nitro;

(o) cyano;

(p) —C(O)H or —C(O)$Z^6$;

(q) —CO$_2$H or —CO$_2Z^6$;

(r) —$Z^4$—$NZ^7Z^8$;

(s) —$Z^4$—N($Z^{11}$)—$Z^5$—H;

(t) —$Z^4$—N($Z^{11}$)—$Z^5$—$Z^6$; or (u) —$Z^4$—N($Z^{11}$)—$Z^5$—$NZ^7Z^8$; $Z^4$ and $Z^5$ are each independently (a) a single bond;

(b) —$Z^9$—S(O)$_n$—$Z^{10}$—;

(c) —$Z^9$—C(O)—$Z^{10}$—;
(d) —$Z^9$—C(S)—$Z^{10}$—;
(e) —$Z^9$—O—$Z^{10}$—;
(f) —$Z^9$—S—$Z^{10}$—;
(g) —$Z^9$—O—C(O)—$Z^{10}$—; or
(h) —$Z^9$—C(O)—$Z^{10}$—;

$Z^6$ is alkyl; alkyl substituted with one to three groups selected from halogen, aryl, aryloxy and alkoxy; alkenyl; alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy and trihaloalkoxy; or heterocyclo or substituted heterocyclo;

$Z^7$ and $Z^8$ are each independently hydrogen, alkyl, cycloalkyl, cycloalkylalkyl, cycloalkenylalkyl, aryl or aralkyl or $Z^7$ and $Z^8$ together are alkylene or alkenylene, completing a 3- to 8-membered saturated or unsaturated ring together with the nitrogen atom to which they are attached;

$Z^9$ and $Z^{10}$ are each independently a single bond, alkylene, alkenylene or alkynylene;

$Z^{11}$ is
(a) hydrogen; or
(b) alkyl, alkyl substituted with one, two or three halogens, cycloalkyl, cycloalkylalkyl, cycloalkenylalkyl, aryl or aralkyl;

or any two of $Z^7$, $Z^8$ and $Z^{11}$ together are alkylene or alkenylene, completing a 3- to 8-membered saturated or unsaturated ring together with the atoms to which they are attached;

$R^{15}$ is hydrogen, alkyl, hydroxyethoxy methyl or methoxyethoxy methyl;

each m is independently 1 or 2;

each n is independently 0, 1 or 2; and p is 0 or an integer from 1 to 2.

Preferred compounds of the formula I are those having one or more (most preferably, all) of the following preferred substituent definitions:

X is O;

Y is N;

$R^3$ and $R^4$ are alkyl, especially lower alkyl such as methyl;

$R^{11}$, $R^{12}$, $R^{13}$ and $R^{14}$ are each independently hydrogen, hydroxy, amino, heterocyclo, alkenyl, alkoxy, carboxamide, or substituted lower alkyl, especially, $R^{12}$, $R^{13}$ and $R^{14}$ are hydrogen and $R^{11}$ is hydrogen, hydroxy, amino, heterocyclo, alkenyl, alkoxy, carboxamide or substituted lower alkyl;

p is zero;

$R^1$ and $R^2$ are hydrogen or are absent;

Q is N;

K is CH, J is O and the double bond α is present or K is C=O, J is $NR^{15}$ and neither of the double bonds α or β is present;

$R^{15}$ is hydrogen, hydroxyethoxy methyl or methoxyethoxy methyl.

DETAILED DESCRIPTION OF THE INVENTION

Listed below are definitions of terms used in this specification. These definitions apply to the terms as used throughout this specification, individually or as part of another group, unless otherwise indicated in specific instances.

The term "alkyl" or "alk-" refers to straight or branched chain hydrocarbon groups having 1 to 10 carbon atoms, preferably 1 to 7 carbon atoms. The expression "lower alkyl" refers to alkyl groups of 1 to 4 carbon atoms.

The term "alkoxy" refers to alkyl-O-; the term "alkylthio" refers to alkyl-S-. The expression "lower alkoxy" refers to lower alkyl-O-.

The term "aryl" or "ar-" refers to phenyl, naphthyl and biphenyl.

The term "aryloxy" refers to aryl-O-; the term "arylthio" refers to aryl-S-.

The term "alkenyl" refers to straight or branched chain hydrocarbon groups of 2 to 10 carbon atoms having at least one double bond. Groups of two to four carbon atoms are preferred.

The term "alkynyl", refers to straight or branched chain groups of 2 to 10 carbon atoms having at least one triple bond. Groups of two to four carbon atoms are preferred.

The term "alkylene" refers to a straight chain bridge of 1 to 5 carbon atoms connected by single bonds (e.g., —$(CH_2)_x$— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —$CH_2$—CH=CH—, —$CH_2$—CH=CH—$CH_2$—, —$C(CH_3)_2$CH=CH— and —CH($C_2H_5$)—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —$CH_2$—C≡C—, —CH($CH_3$)—C≡C— and —C≡C—CH($C_2H_5$)$CH_2$—.

The term "alkanoyl" refers to groups of the formula —C(O)alkyl.

The terms "cycloalkyl" and "cycloalkenyl" refer to cyclic hydrocarbon groups of 3 to 8 carbon atoms.

The term "hydroxyalkyl" refers to an alkyl group including one or more hydroxy radicals such as —$CH_2CH_2OH$, —$CH_2CH(OH)CH_2OH$, —$CH(CH_2OH)_2$ and the like.

The terms "halogen" and "halo" refer to fluorine, chlorine, bromine and iodine.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms or sulfur atoms, where the nitrogen and sulfur heteroatoms may optionally be oxidized and the nitrogen heteroatoms may optionally be quaternized. The heterocyclic group may be attached at any heteroatom or carbon atom.

Exemplary monocyclic heterocyclic groups include pyrrolidinyl, pyrrolyl, pyrazolyl, oxetanyl, pyrazolinyl imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b] pyridinyl), dihydroisoindolyl, dihydroquinazolinyl (such as 3,4-dihydro-4-oxo-quinazolinyl) and the like.

Exemplary tricyclic heterocyclic groups include carbazolyl, benzidolyl, phenanthrolinyl, acridinyl, phenanthridinyl, xanthenyl and the like.

The expression "substituted heterocyclo" refers to a heterocycle substituted with 1, 2 or 3 of the following:

(a) alkyl, especially lower alkyl;
(b) hydroxy (or protected hydroxy);
(c) halo;
(d) oxo (i.e.=O);
(e) amino, alkylamino or dialkylamino;
(f) alkoxy;
(g) carbocyclo, such as cycloalkyl or cycloalkenyl;
(h) carboxy;
(i) heterocyclooxy;
(j) alkoxycarbonyl, such as lower alkoxycarbonyl;
(k) carbamyl (i.e., $H_2N-C(O)-$), alkylcarbamyl or dialkylcarbamyl;
(l) mercapto;
(m) nitro;
(n) cyano;
(o) sulfonamido (i.e., $NH_2-SO_2-$), sulfonamidoalkyl or sulfonamidodialkyl;
(p)

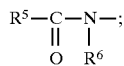

(q)

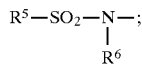

(r) aryl;
(s) alkylcarbonyloxy;
(t) arylcarbonyloxy;
(u) arylthio;
(v) aryloxy;
(w) alkylthio;
(x) formyl;
(y) arylalkyl; or
(z) aryl substituted with alkyl, cycloalkyl, alkoxy, hydroxy, amino, alkylamino, dialkylamino, halo or trihaloalkyl.

The term "heterocyclooxy" denotes a heterocyclic group bonded through an oxygen bridge.

The term "salt(s)" denotes acidic and/or basic salts formed with inorganic and/or organic acids and bases. Zwitterions (internal or inner salts) are included within the term "salt(s)" as used herein, as are quaternary ammonium salts such as alkylammonium salts.

Throughout the specification, groups and substituents thereof are chosen to provide stable moieties and compounds.

The compounds of formula I form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, t-butyl amine, benzathine, N-methyl-D-glucamide and hydrabamine, and with amino acids such as arginine, lysine and the like. Such salts may be obtained by reacting compound I with the desired ion in a medium in which the salt precipitates or in an aqueous medium followed by lyophilization.

When the $R^1$ to $R^4$ or $R^{11}$ to $R^{14}$ substituents comprise a basic moiety, such as amino or substituted amino, compound I may form salts with a variety of organic and inorganic acids. Such salts include those formed with hydrochloric acid, hydrogen bromide, methanesulfonic acid, sulfuric acid, acetic acid, maleic acid, benzenesulfonate, toluenesulfonate and various other sulfonates, nitrates, phosphates, borates, acetates, tartrates, maleates, citrates, succinates, benzoates, ascorbates, salicylates and the like. Such salts may be formed by reacting compound I in an equivalent amount of the acid in a medium in which the salt precipitates or in an aqueous medium followed by lyophilization.

In addition, when the $R^1$ to $R^4$ or $R^{11}$ to $R^{14}$ substituents comprise a basic moiety such as amino, zwitterions may be formed.

All stereoisomeric forms of the compounds of the formula I and salts thereof are contemplated in the present invention, whether present as a single enantiomer or diastereomer free of other stereoisomers, a racemic mixture, or a mixture of all other or other selected stereoisomeric forms thereof. Especially, certain of the $R^1$ to $R^4$ and $R^{11}$ to $R^{14}$ substituents of compound I may contain asymmetric carbon atoms. Such compounds of formula I may exist, therefore, in enantiomeric and diastereomeric forms and in racemic mixtures thereof. All are within the scope of this invention. Additionally, compound I may exist as enantiomers even in the absence of asymmetric carbons. All such enantiomers are within the scope of this invention. 5 The compounds of formula I are antagonists of ET-1, ET-2 and/or ET-3 and are useful in treatment of conditions associated with increased ET levels (e.g., dialysis, trauma and surgery) and of all endothelin-dependent disorders. They are thus useful as antihypertensive agents. By the administration of a composition having one (or a combination) of the compounds of this invention, the blood pressure of a hypertensive mammalian (e.g., human) host is reduced. They are also useful in pregnancy-induced hypertension and coma (preeclampsia and eclampsia), acute portal hypertension and hypertension secondary to treatment with erythropoietin.

The compounds of the present invention are also useful in the treatment of disorders related to renal, glomerular and mesangial cell function, including acute and chronic renal failure, glomerular injury, renal damage secondary to old age or related to dialysis, nephrosclerosis (especially hypertensive nephrosclerosis), nephrotoxicity (including nephrotoxicity related to imaging and contrast agents and to cyclosporine), renal ischemia, primary vesicoureteral reflux, glomerulosclerosis and the like. The compounds of this invention may also be useful in the treatment of disorders related to paracrine and endocrine function.

The compounds of the present invention are also useful in the treatment of endotoxemia or endotoxin shock as well as hemorrhagic shock.

The compounds of the present invention are also useful in hypoxic and ischemic disease and as anti-ischemic agents for the treatment of, for example, cardiac, renal and cerebral ischemia and reperfusion (such as that occurring following cardiopulmonary bypass surgery), coronary and cerebral vasospasm, and the like.

In addition, the compounds of this invention may also be useful as anti-arrhythmic agents; anti-anginal agents; anti-fibrillatory agents; anti-asthmatic agents; anti-atherosclerotic and anti-arteriosclerotic agents; additives to cardioplegic solutions for cardiopulmonary bypasses; adjuncts to thrombolytic therapy; and anti-diarrheal agents. The compounds of this invention may be useful in therapy for myocardial infarction; therapy for peripheral vascular disease (e.g., Raynaud's disease and Takayashu's disease); treatment of cardiac hypertrophy (e.g., hypertrophic cardiomyopathy); treatment of primary pulmonary hypertension (e.g., plexogenic, embolic) in adults and in the newborn and pulmonary hypertension secondary to heart failure, radiation and chemotherapeutic injury, or other trauma; treatment of central nervous system vascular disorders, such as stroke, migraine and subarachnoid hemorrhage; treatment of central nervous system behavioral disorders; treatment of gastrointestinal diseases such as ulcerative colitis, Crohn's disease, gastric mucosal damage, ulcer and ischemic bowel disease; treatment of gall bladder or bile duct-based diseases such as cholangitis; treatment of pancreatitis; regulation of cell growth; treatment of benign prostatic hypertrophy; restenosis following angioplasty or following any procedures including transplantation; therapy for congestive heart failure including inhibition of fibrosis; inhibition of left ventricular dilatation, remodeling and dysfunction; and treatment of hepatotoxicity and sudden death. The compounds of this invention may be useful in the treatment of sickle cell disease including the initiation and/or evolution of the pain crises of this disease; treatment of the deleterious consequences of ET-producing tumors such as hypertension resulting from hemangiopericytoma; treatment of early and advanced liver disease and injury including attendant complications (e.g., hepatotoxicity, fibrosis and cirrhosis); treatment of spastic diseases of the urinary tract and/or bladder; treatment of hepatorenal syndrome; treatment of immunological diseases involving vasculitis such as lupus, systemic sclerosis, mixed cryoglobulinemia; and treatment of fibrosis associated with renal dysfunction and hepatotoxicity. The compounds of this invention may be useful in therapy for metabolic and neurological disorders; cancer; insulin-dependent and non insulin-dependent diabetes mellitus; neuropathy; retinopathy; maternal respiratory distress syndrome; dysmenorrhea; epilepsy; hemorrhagic and ischemic stroke; bone remodeling; psoriasis; and chronic inflammatory diseases such as rheumatoid arthritis, osteoarthritis, sarcoidosis and eczematous dermatitis (all types of dermatitis).

The compounds of this invention can also be formulated in combination with endothelin converting enzyme (ECE) inhibitors, such as phosphoramidon; thromboxane receptor antagonists; potassium channel openers; thrombin inhibitors (e.g., hirudin and the like); growth factor inhibitors such as modulators of PDGF activity; platelet activating factor (PAF) antagonists; angiotensin II (AII) receptor antagonists; renin inhibitors; angiotensin converting enzyme (ACE) inhibitors such as captopril, zofenopril, fosinopril, ceranapril, alacepril, enalapril, delapril, pentopril, quinapril, ramipril, lisinopril and salts of such compounds; neutral endopeptidase (NEP) inhibitors; dual NEP-ACE inhibitors; HMG CoA reductase inhibitors such as pravastatin and mevacor; squalene synthetase inhibitors; bile acid sequestrants such as questran; calcium channel blockers; potassium channel activators; beta-adrenergic agents; antiarrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; and thrombolytic agents such as tissue plasminogen activator (tPA), recombinant tPA, streptokinase, urokinase, prourokinase and anisoylated plasminogen streptokinase activator complex (APSAC). If formulated as a fixed dose, such combination products employ the compounds of this invention within the dosage range described below and the other pharmaceutically active agent within its approved dosage range. The compounds of this invention may also be formulated with, or useful in conjunction with, antifungal and immunosuppressive agents such as amphotericin B, cyclosporins and the like to counteract the glomerular contraction and nephrotoxicity secondary to such compounds. The compounds of this invention may also be used in conjunction with hemodialysis.

The compounds of the invention can be administered orally or parenterally to various mammalian species known to be subject to such maladies, e.g., humans, in an effective amount within the dosage range of, especially, about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The present invention provides pharmaceutical compositions for the treatment of endothelin-related disorders comprising a compound of the formula I or pharmaceutically acceptable salt thereof and a pharmaceutically acceptable vehicle or diluent. The active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice.

The compounds of the invention may also be administered topically to treat peripheral vascular diseases and as such may be formulated as a cream or ointment.

The compounds of formula I can also be formulated in compositions such as sterile solutions or suspensions for parenteral administration. About 0.1 to 500 milligrams of a compound of formula I is compounded with a physiologically acceptable vehicle, carrier, excipient, binder, preservative, stabilizer, etc., in a unit dosage form as called for by accepted pharmaceutical practice. The amount of active substance in these compositions or preparations is such that a suitable dosage in the range indicated is obtained.

The compounds of the present invention may be prepared as follows.

SCHEME I

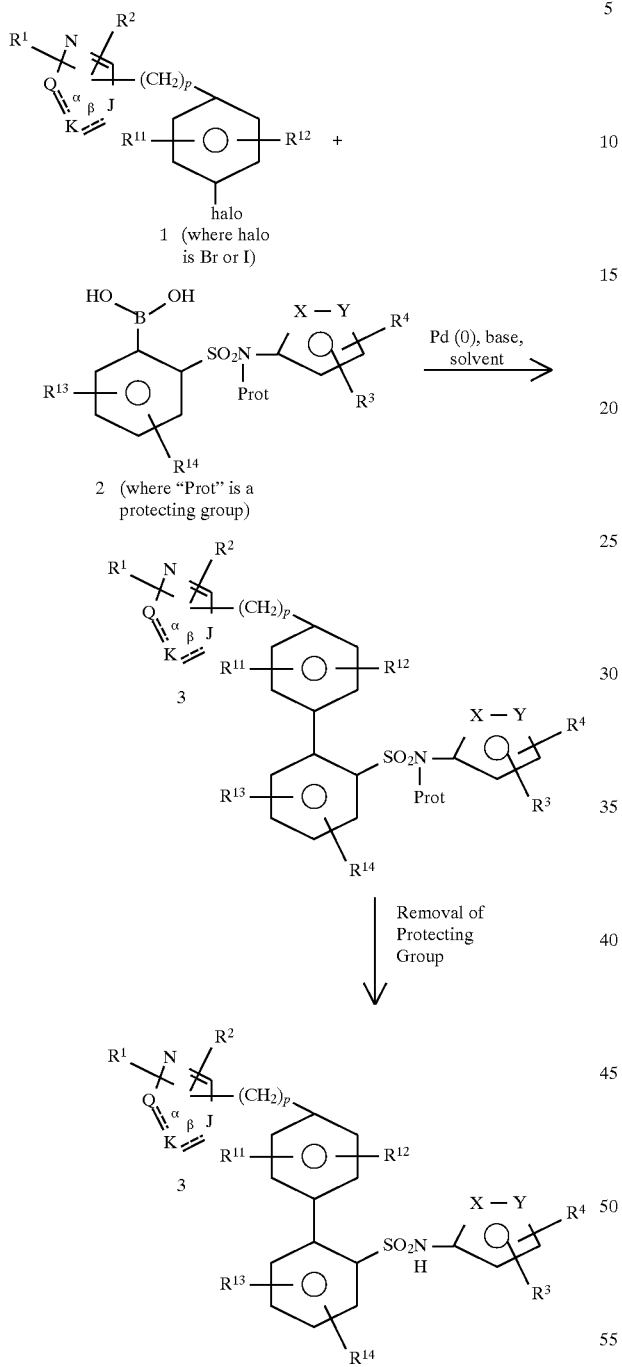

1 (where halo is Br or I)

2 (where "Prot" is a protecting group)

As depicted by the above Scheme I, the title compounds of the formula I may be prepared by a Pd(O) catalyzed coupling of an appropriately protected phenylsulfonamide-2-boronic acid intermediate 2 with a 4-heterocyclic aryl halide 1 in the presence of a suitable base, such as aqueous potassium carbonate, and solvent, such as a mixture of toluene and ethanol.

A boronic acid intermediate 2 may be prepared from a 2-bromophenylsulfonamide 4 (preparation of which is described in European Patent Application Publication No. 0,569,193 (1993)) by lithiation with a suitable alkyl lithium (such as n-butyl lithium), subsequent treatment with a trialkylborate (e.g., triisopropyl borate) and finally adding an aqueous acid such as aqueous hydrochloric acid (SCHEME II):

SCHEME II

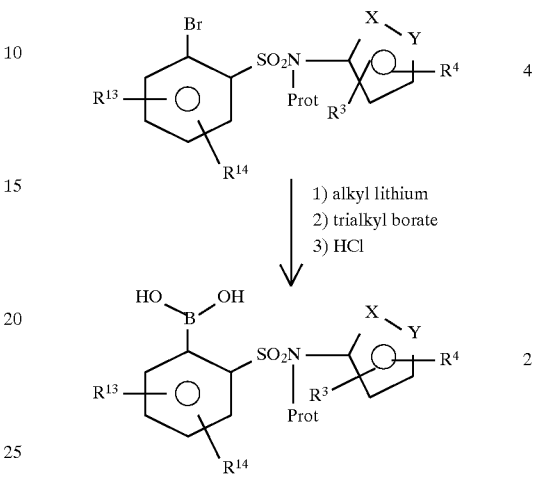

"Prot" is an appropriate protecting group for the sulfonamide function, also described in European Patent Application Publication No. 0,569,193 (1993).

4-Heterocyclic aryl halide intermediate 1 may be prepared by methods known in the art, for example, those methods described in Lyga, *Syn. Commun.*, 16(2), 163–167 (1986) and *J. Het. Chem.*, 26, 125 (1989).

The title compounds may also be synthesized by an alternate route shown below (SCHEME III):

SCHEME III

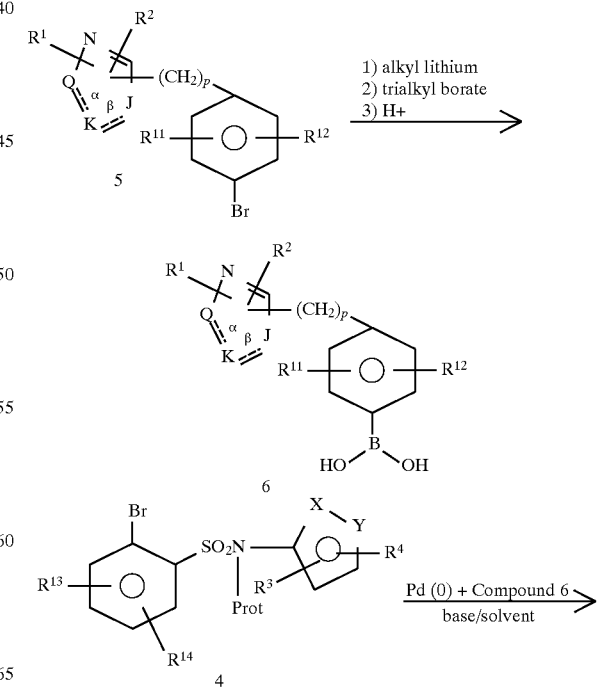

-continued
SCHEME III

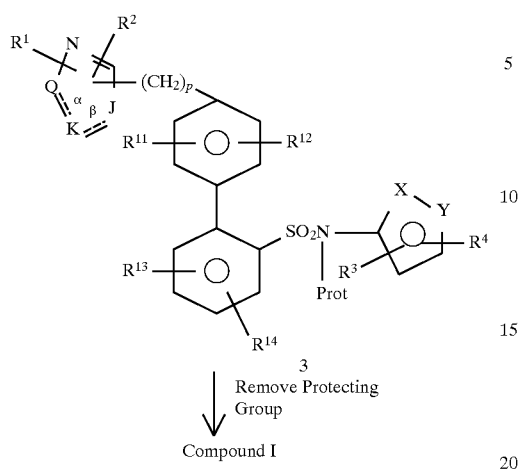

↓ 3 Remove Protecting Group

Compound I

As depicted above, a 4'-heterocyclic aryl halide 5 (see compound 1 where halo is Br) can be converted to a boronic acid intermediate 6 via the sequence shown. This compound 6, upon Pd(O) catalyzed coupling with a compound 4 can provide a biaryl analog 3, which upon deprotection can lead to the title compound I. In certain instances, the heteroatoms of the heterocyclic ring bonded directly to the group —(CH$_2$)p— may be protected to prepare the boronic acid 6, and/or to facilitate the coupling reaction to make compound 3. For example, when one or more of the heteroatoms of this heterocyclic ring are N, one of the groups may be protected by a suitable protecting group such as t-butoxycarbonyl, etc. Also, in certain instances, the boronic acid may be replaced with a tin species to perform the coupling reaction. For general strategies in biaryl synthesis, see: Bringmann et al., *Angew. Chem. Inst.*, Ed. Engl. 29 (1990) 977–991.

In the above schemes, specific $R^{11}$–$R^{14}$ groups are chosen to be compatible with the reaction conditions shown. Additionally, specific $R^{11}$–$R^{14}$ groups may be converted into alternative $R^{11}$–$R^{14}$ groups, either before or after coupling of Compound 1 with Compound 2, or Compound 4 with Compound 6, using methods known in the art.

The compounds of the present invention may also be prepared by methods described in or analogous to those described in U.S. patent application Ser. No. 08/603,975, filed Feb. 20, 1996 by Murugesan et al. (Attorney Docket No. HA662d) entitled "Substituted Biphenyl Isoxazole Sulfonamides" and/or U.S. patent application Ser. No. 60,011,974, filed Feb. 20, 1996 by Polniaszek et al. (Attorney Docket No. HA689*) entitled "Methods for the Preparation of Biphenyl Isoxazole Sulfonamides", each incorporated herein by reference in its entirety.

The invention will now be further described by the following working examples, which are preferred embodiments of the invention. These examples are meant to be illustrative rather than limiting.

EXAMPLE 1

4'-[4,5-Dihydro-4-[(2-methoxyethoxy)methyl]-5-oxo-1H-1,2,4-triazol-1-yl]-N-(3,4-dimethyl-5-isoxazolyl)[1,1'-biphenyl]-2-sulfonamide

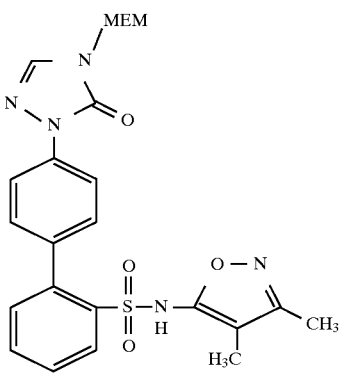

A. [(4-Bromophenyl)hydrazono]acetic acid

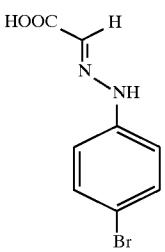

To a solution of (4-bromophenyl)hydrazine (5.0 g, 22.37 mmol) in 30 ml of 10% aqueous hydrochloric acid, a solution of glyoxylic acid monohydrate (2.06 g, 22.37 mmol) in 5 ml of water was added and the mixture stirred overnight at room temperature. The light brown solid was filtered and dried (3.6 g, 54%).

B. 2-(4-Bromophenyl)-2,4-dihydro-3H-1,2,4-triazol-3-one

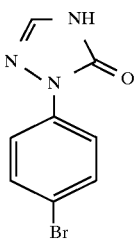

To the product of Step (A) (3.5 g, 11.76 mmol) in 100 ml toluene was added triethyl amine (1.19 g, 11.76 mmol) and diphenylphosphoryl azide (3.23 g, 11.74 mmol) and the mixture was refluxed for 1.5 hrs. The solution was then poured into 150 ml of 5% aqueous KOH and stirred for 10 min. The aqueous layer was separated and acidified to pH 1 using hydrochloric acid. The mixture was then extracted with 3×100 ml ethyl acetate (EtOAc). The combined organic extracts were then dried and evaporated to provide 1.1 g (39%) of the title product of this step as a light yellow solid.

C. 2-(4-Bromophenyl)-2,4-dihydro-4-[(2-methoxyethoxy)methyl]-3H-1,2,4-triazol-3-one

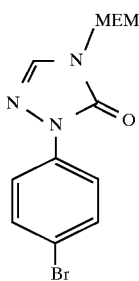

To the product of Step (B) (240 mg, 1.0 mmol) in 10 ml tetrahydrofuran (THF), NaH (60% in mineral oil, 54 mg, 1.35 mmol) was added. The mixture was stirred at room temperature for 15 min. Methoxyethoxy methyl chloride (156 mg, 1.25 mmol) ("MEM" denotes methoxyethoxy methyl herein) was added dropwise. The reaction was stirred at room temperature for 3 hrs., and concentrated. 50 ml EtOAc was added and the organic liquid was washed with 5 ml H$_2$O and 5 ml brine, dried and concentrated. The residue was chromatographed on silica gel using 3:2 hexane/ EtOAc to afford the title product of this step (215 mg, 66%).
D. 4'-[4,5-Dihydro-4-[(2-methoxyethoxy)methyl ]-5-oxo-1H-1,2,4-triazol-1-yl]-N-(3,4-dimethyl-5-isoxazolyl)-N-[(2-methoxyethoxy)methyl][1,1'-biphenyl]-2-sulfonamide

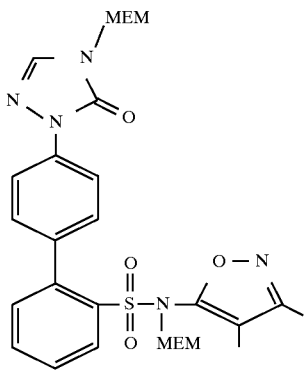

To a solution of 2-borono-N-(3,4-dimethyl-5-isoxazolyl)-N-[(2-methoxyethoxy)methyl]-benzenesulfonamide (378 mg, 0.98 mmol, prepared as described in U.S. patent application Ser. No. 08/603,975, filed Feb. 20, 1996 by Murugesan et al. (Attorney Docket No. HA662d) entitled "Substituted Biphenyl Isoxazole Sulfonamides"), the product of Step (C) (215 mg, 0.66 mmol) in 7.5 ml of toluene and 6 ml of 95% ethyl alcohol (EtOH) under argon, tetrakis (triphenylphosphine)-palladium(0) (76 mg, 0.066 mmol) was added and followed by 4.5 ml of 2M aq. sodium carbonate. The reaction mixture was heated at 75° C. for 3.5 hrs., cooled and diluted with 40 ml of EtOAc. The organic liquid was separated and washed with 10 ml H$_2$O and 10 ml brine, dried and concentrated. The residue was chromatographed on silica gel using 1:7 hexane/EtOAc to afford the title product of this step (280 mg, 73%) as a colorless gum. R$_f$=0.19, silica gel, 1:9 hexane/EtOAc.
E. 4'-[4,5-Dihydro-4-[(2-methoxyethoxy)methyl]-5-oxo-1H-1,2,4-triazol-1-yl]-N-(3,4-dimethyl-5-isoxazolyl)[1,1'-biphenyl]-2-sulfonamide To a solution of the product of Step (D) (130 mg, 0.22 mmol) in 5 ml of 95% EtOH, 5 ml of 6N aq. HCl was added and refluxed for 2 hrs. The reaction mixture was concentrated and the pH of the solution was adjusted to 8 using sodium bicarbonate solution. It was then reacidified to pH 5 with glacial acetic acid, and extracted with 3×20 ml CH$_2$Cl$_2$. The organic extracts were washed with 5 ml H$_2$O and dried and concentrated to give the title product of this Example.

melting point (mp)=81°–84° C.

EXAMPLE 2

4'-[4,5-Dihydro-4-[(2-hydroxyethoxy)methyl]-5-oxo-1H-1,2,4-triazol-1-yl]-N-(3,4-dimethyl-5-isoxazolyl)[1,1'-biphenyl]-2-sulfonamide

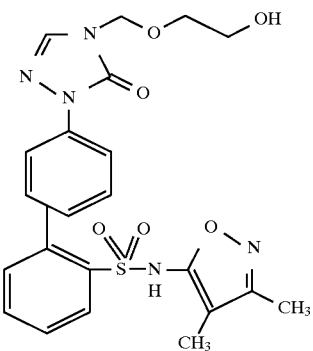

To a solution of the title product of Example 1 (130 mg, 0.22 mmol) in 2.2 ml CH$_3$CN at 0° C., trimethylsilyl chloride (Me$_3$SiCl) (143 mg, 1.32 mmol) was added followed by NaI (198 mg, 1.32 mmol). The mixture was stirred at room temperature for 3 hrs. 5 ml H$_2$O was added and extracted with 50 ml EtOAc. The organic liquid was washed with 5 ml sat. aqueous Na$_2$S$_2$O$_3$ and 5 ml brine, dried and concentrated. The residue was purified by preparative HPLC on a 30×500 mm ODS S10 column using 53% solvent A (10% methanol (MeOH), 90% H$_2$O, 0.1% trifluoroacetic acid (TFA)) and 47% solvent B (90% MeOH, 10% H$_2$O, 0.1% TFA) to provide the title product of this Example (30 mg, 28% for two steps) as a white solid.

m.p. 80°–90° C. (amorphous), Rf=0.29, silica gel, 10:1 CH$_2$Cl$_2$/MeOH.

EXAMPLE 3

N-(3,4-Dimethyl-5-isoxazolyl)-4'-(1,3,4-oxadiazol-2-yl) [1,1'-biphenyl]-2-sulfonamide

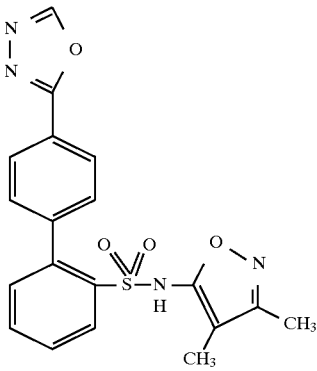

A. 2-(4-Bromophenyl)-1,3,4-oxadiazole

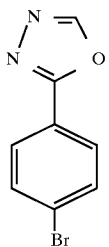

To hydrazinecarboxaldehyde (1.20 g, 20 mmol) in 100 ml THF, triethylamine (Et$_3$N) (2.63 g, 26 mmol) was added. The mixture was heated at 60° C. to a clear solution and cooled to room temperature. 4-Bromobenzoyl chloride (4.39 g, 20 mmol) was added to the reaction mixture over 20 min. The mixture was refluxed for 1 hr., cooled to room temperature and filtered. The filtrate was concentrated to give a light yellow solid (2-[(4-bromophenyl)carbonyl]-hydrazinecarboxaldehyde).

A mixture of 2-[(4-bromophenyl) carbonyl]-hydrazinecarboxaldehyde and 8 g P$_2$O$_5$ was heated at 110° C. for 40 hrs. The resulting solid was cooled to room temperature and then mixed with 150 g crushed ice and neutralized with aqueous NaOH. The mixture was extracted with 3×150 ml EtOAc and the organic liquid was washed with 75 ml H$_2$O and 75 ml brine, dried and concentrated. The residue was chromatographed on silica gel using 10:3 hexane/EtOAc to afford the title product of this step (1.48 g, 33% for two steps) as a white solid. R$_f$=0.27, silica gel, 3:1 hexane/EtOAC.

B. N-(3,4-Dimethyl-5-isoxazolyl)-N-[(2-methoxyethoxy)methyl]-4'-(1,3,4-oxadiazol-2-yl)[1,1'-biphenyl]-2-sulfonamide

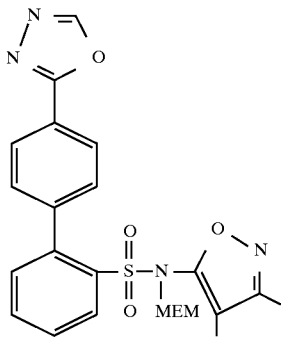

To a solution of 2-borono-N-(3,4-dimethyl-5-isoxazolyl)-N-[(2-methoxyethoxy) methyl]-benzenesulfonamnide (576 mng, 1.5 mnmol, see Step (D) of Example 1), the product of Step (A) (439 mg, 1.95 mmol) in 13.5 ml of toluene and 10.8 ml of 95% EtOH under argon, tetrakis(triphenylphosphine)-palladium(0) (173 mg, 0.15 mmol) was added and followed by 8.1 ml of 2M aq. sodium carbonate. The reaction mixture was heated at 75° C. for 50 min., cooled and diluted with 80 ml of EtOAc. The organic liquid was separated and washed with 20 ml H$_2$O and 20 ml brine, dried and concentrated. The residue was chromatographed on silica gel using 1:1 hexane/EtOAc to afford the title product of this step (510 mg, 70%) as a colorless gum. R$_f$=0.33, silica gel, 1:2 hexane/EtOAC.

C. N-(3,4-Dimethyl-5-isoxazolyl)-4'-(1,3,4-oxadiazol-2-yl)[1,1'-biphenyl]-2-sulfonamide To a solution of the product of Step (B) (510 mg, 1.05 mmol) in 5.3 ml CH$_3$CN at 0° C. Me$_3$SiCl (686 mg, 6.32 mmol) was added followed by NaI (946 mg, 6.32 mmol). The mixture was stirred at room temperature for 1 hr. 10 ml H$_2$O was added and extracted with 100 ml EtOAc. The organic extracts were washed with 10 ml sat. aqueous Na$_2$S$_2$O$_3$ and 10 ml brine, dried and concentrated. The residue was chromatographed on silica gel using 1:3 CH$_2$Cl$_2$/EtOAc and then EtOAc to afford the title product of this Example (216 mg, 52%) as a white solid.

m.p.>165° C., dec.
Analysis calculated for C$_{19}$H$_{16}$N$_4$O$_4$S·0.13 H$_2$O
Calc'd: C, 57.22; H, 4.11; N, 14.05; S, 8.04.
Found: C, 57.01; H, 3.95; N, 13.72; S, 7.76.

What is claimed is:

1. A compound of the formula

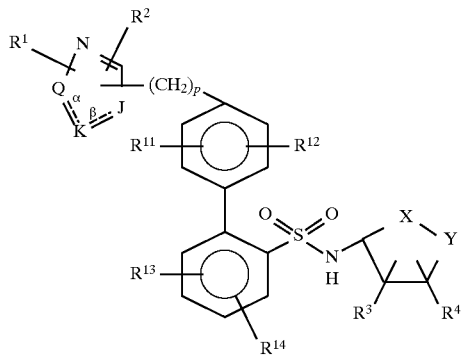

or an enantiomer, diastereomer or pharmaceutically acceptable salt thereof,
wherein:
one of X and Y is N and the other is O;
Q is N or NR$^{15}$;
J is O, S, N or NR$^{15}$;
K is C=O or CH;
the dotted line α between Q and K denotes an optional double bond when Q is N and K is CH;
the dotted line β between K and J denotes an optional double bond when K is CH and J is N;
with the proviso that said α and β double bonds may not simultaneously be present;
R$^1$ and R$^2$, when present, and R$^3$ and R$^4$, are each directly bonded to a ring carbon and are each independently
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with Z$^1$, Z$^2$ and Z$^3$;
(c) halo;
(d) hydroxyl;
(e) cyano;
(f) nitro;
(g) —C(O)H or —C(O)R$^5$;
(h) —CO$_2$H or —CO$_2$R$^5$;
(i) —Z$^4$—NR$^6$R$^7$; or
(j) —Z$^4$—N(R$^{10}$)—Z$^5$—NR$^8$R$^9$; or
(k) R$^3$ and R$^4$ together are alkylene or alkenylene, either of which may be substituted with Z$^1$, Z$^2$ and Z$^3$, completing a 4- to 8-membered saturated, unsaturated or aromatic ring together with the carbon atoms to which they are attached;
R$^5$ is alkyl, alkenyl, alkynyl, cycloalkyl, cycloalkylalkyl, cycloalkenyl, cycloalkenylalkyl, aryl or aralkyl, any of which may be substituted with Z$^1$, Z$^2$ and Z$^3$;

$R^6$, $R^7$, $R^8$, $R^9$ and $R^{10}$ are each independently
  (a) hydrogen; or
  (b) alkyl, cycloalkyl, cycloalkylalkyl, cycloalkenylalkyl, aryl or aralkyl, any of which may be substituted with $Z^1$, $Z^2$ and $Z^3$; or
$R^6$ and $R^7$ together are alkylene or alkenylene, either of which may be substituted with $Z^1$, $Z^2$ and $Z^3$, completing a 3- to 8-membered saturated or unsaturated ring together with the nitrogen atom to which they are attached; or any two of $R^8$, $R^9$ and $R^{10}$ together are alkylene or alkenylene, either of which may be substituted with $Z^1$, $Z^2$ and $Z^3$, completing a 3- to 8-membered saturated or unsaturated ring together with the atoms to which they are attached;
$R^{11}$, $R^{12}$, $R^{13}$ and $R^{14}$ are each independently
  (a) hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$,
  (c) heterocyclo, substituted heterocyclo or heterocyclooxy;
  (d) halo;
  (e) hydroxyl;
  (f) cyano;
  (g) nitro;
  (h) —C(O) H or —C(O)$R^5$;
  (i) —CO$_2$H or —CO$_2R^5$;
  (j) —SH, —S(O)$_n R^5$, —S(O)$_m$—OH, —S(O)$_m$—OR$^5$, —O—S(O)$_m$—OR$^5$, —O—S(O)$_m$OH or —O—S(O)$_m$—OR$^5$;
  (k) —Z$^4$—NR$^6$R$^7$; or
  (l) —Z$^4$—N(R$^{10}$)—Z$^5$—NR$^8$R$^9$; $Z^1$, $Z^2$ and $Z^3$ are each independently
  (a) hydrogen;
  (b) halo;
  (c) hydroxy;
  (d) alkyl;
  (e) alkenyl;
  (f) aryl;
  (g) aralkyl;
  (h) alkoxy;
  (i) aryloxy;
  (j) aralkoxy;
  (k) heterocyclo, substituted heterocyclo or heterocyclooxy,
  (l) —SH, —S(O)$_n Z^6$, —S(O)$_m$—OH, —S(O)$_m$—OZ$^6$, —O—S(O)$_m$—Z$^6$, —O—S(O)$_m$OH or —O—S(O)$_m$—OZ$^6$;
  (m) oxo;
  (n) nitro;
  (o) cyano;
  (p) —C(O)H or —C(O)Z$^6$;
  (q) —CO$_2$H or —CO$_2$Z$^6$;
  (r) —Z$^4$—NZ$^7$Z$^8$;
  (s) —Z$^4$—N(Z$^{11}$)—Z$^5$—H;
  (t) —Z$^4$—N(Z$^{11}$)—Z$^5$—Z$^6$; or
  (u) —Z$^4$—N(Z$^{11}$)—Z$^5$—Z$^7$Z$^8$;
$Z^4$ and $Z^5$ are each independently
  (a) a single bond;
  (b) —Z$^9$—S(O)$_n$—Z$^{10}$—;
  (c) —Z$^9$—C(O)—Z$^{10}$—;
  (d) —Z$^9$—C(S)—Z$^{10}$—;
  (e) —Z$^9$—O—Z$^{10}$—;
  (f) —Z$^9$—S—Z$^{10}$—;
  (g) —Z$^9$—O—C(O)—Z$^{10}$—; or
  (h) —Z$^9$—C(O)—O—Z$^{10}$—;

$Z^6$ is alkyl; alkyl substituted with one to three groups selected from halogen, aryl, aryloxy and alkoxy; alkenyl; alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy and trihaloalkoxy; or heterocyclo or substituted heterocyclo;

$Z^7$ and $Z^8$ are each independently hydrogen, alkyl, cycloalkyl, cycloalkylalkyl, cycloalkenylalkyl, aryl or aralkyl or $Z^7$ and $Z^8$ together are alkylene or alkenylene, completing a 3- to 8-membered saturated or unsaturated ring together with the nitrogen atom to which they are attached;

$Z^9$ and $Z^{10}$ are each independently a single bond, alkylene, alkenylene or alkynylene;

$Z^{11}$ is
  (a) hydrogen; or
  (b) alkyl, alkyl substituted with one, two or three halogens, cycloalkyl, cycloalkylalkyl, cycloalkenylalkyl, aryl or aralkyl;
or any two of $Z^7$, $Z^8$ and $Z^{11}$ together are alkylene or alkenylene, completing a 3- to 8-membered saturated or unsaturated ring together with the atoms to which they are attached;

$R^{15}$ is hydrogen, alkyl, hydroxyethoxy methyl or methoxyethoxy methyl;

each m is independently 1 or 2;

each n is independently 0, 1 or 2; and p is 0 or an integer from 1 to 2.

2. A compound of claim 1, wherein X is O and Y is N.

3. A compound of claim 1, wherein $R^3$ and $R^4$ are each independently alkyl.

4. A compound of claim 3, wherein $R^3$ and $R^4$ are each methyl.

5. A compound of claim 1, wherein $R^{11}$, $R^{12}$, $R^{13}$ and $R^{14}$ are each independently hydrogen, hydroxy, amino, heterocyclo, alkenyl, alkoxy, carboxamide, or substituted lower alkyl.

6. A compound of claim 5, wherein $R^{12}$, $R^{13}$ and $R^{14}$ are hydrogen and $R^{11}$ is hydrogen, hydroxy, amino, heterocyclo, alkenyl, alkoxy, carboxamide or substituted lower alkyl.

7. A compound of claim 1, wherein $R^1$ and $R^2$ are hydrogen or are absent.

8. A compound of claim 1, wherein Q is N.

9. A compound of claim 1, wherein K is CH, J is O and the double bond α is present.

10. A compound of claim 1, wherein K is C=O, J is NR$^{15}$ and neither of the double bonds α or β is present.

11. A compound of claim 1, wherein p is 0.

12. A compound of claim 1, wherein $R^{15}$ is hydroxyethoxy methyl or methoxyethoxy methyl.

13. A compound of claim 1, selected from the group consisting of:

4'-[4,5-dihydro-4-[(2-methoxyethoxy) methyl]-5-oxo-1H-1,2,4-triazol-1-yl ]-N-(3,4-dimethyl-5-isoxazolyl)[1,1'-biphenyl]-2-sulfonamide;

4'-[4,5-dihydro-4-[(2-hydroxyethoxy)methyl ]-5-oxo-1H-1,2,4-triazol-1-yl]-N-(3,4-dimethyl-5-isoxazolyl)[1,1'-biphenyl ]-2-sulfonamide;

N-(3,4-dimethyl-5-isoxazolyl)-4'-(1,3,4-oxadiazol-2-yl)[1,1'-biphenyl]-2-sulfonamide; and salts thereof.

14. A method of treating endothelin-related disorders in a mammal, which comprises administering to said mammal an effective endothelin-related disorder treating amount of a compound of claim 1.

15. A method of treating hypertension, which comprises administering an effective hypertension treating amount of a compound of claim 1.

16. A method of treating pulmonary hypertension, which comprises administering an effective pulmonary hypertension treating amount of a compound of claim 1.

17. A method of treating renal, glomerular or mesangial cell disorders, which comprises administering an effective renal, glomerular or mesangial cell disorder treating amount of a compound of claim 1.

18. A method of treating endotoxemia, which comprises administering an effective endotoxemia treating amount of a compound of claim 1.

19. A method of treating ischemia, which comprises administering an effective ischemia treating amount of a compound of claim 1.

20. A method of inhibiting cell growth, which comprises administering an effective cell growth inhibiting amount of a compound of claim 1.

21. A method of treating atherosclerosis, which comprises administering an effective atherosclerosis treating amount of a compound of claim 1.

22. A method of treating restenosis, which comprises administering an effective restenosis treating amount of a compound of claim 1.

23. A method of treating subarachnoid hemorrhage, which comprises administering an effective subarachnoid hemorrhage treating amount of a compound of claim 1.

24. A method of treating benign prostatic hypertrophy, which comprises administering a benign prostatic hypertrophy treating amount of a compound of claim 1.

25. A method of treating congestive heart failure, which comprises administering an effective congestive heart failure treating amount of a compound of claim 1.

26. The method of claim 14, wherein said compound of claim 1 is used in combination with at least one angiotensin II receptor antagonist, renin inhibitor, angiotensin converting enzyme inhibitor, or dual neutral endopeptidase ACE inhibitor.

27. A pharmaceutical composition for the treatment of an endothelin-related disorder, comprising a compound of claim 1 in an amount effective therefor and a physiologically acceptable vehicle or carrier.

28. A pharmaceutical composition of claim 27, further comprising at least one angiotensin II receptor antagonist, renin inhibitor, angiotensin converting enzyme inhibitor, or dual neutral endopeptidase ACE inhibitor.

* * * * *

UNITED STATES PATENT AND TRADEMARK OFFICE
CERTIFICATE OF CORRRECTION

Page 1 of 7

PATENT NO.   : 5,846,985
DATED        : Dec. 8, 1998
INVENTOR(S)  : Natesan Murugesan It is certified that error appears in the above-identified patent and that said Letters Patent is hereby corrected as shown below:

Title page, item [56] insert the following:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 2 | 8 | 8 | 8 | 4 | 5 | 5 | 5/26/59 | Kano et al. | | | |
| | | 4 | 4 | 1 | 5 | 4 | 9 | 6 | 11/15/83 | Harris et al. | | | |
| | | 4 | 6 | 6 | 1 | 4 | 7 | 9 | 4/87 | Wyvratt, Jr. et al. | | | |
| | | 5 | 2 | 3 | 6 | 9 | 2 | 8 | 8/17/93 | Chakravarty et al. | | | |
| | | 5 | 2 | 7 | 0 | 3 | 1 | 3 | 12/14/93 | Burri et al. | | | |
| | | 5 | 2 | 9 | 2 | 7 | 4 | 0 | 3/8/94 | Burri et al. | | | |
| | | 5 | 3 | 7 | 8 | 7 | 1 | 5 | 1/3/95 | Stein et al. | | | |
| | | 5 | 4 | 6 | 4 | 8 | 5 | 3 | 11/7/95 | Chan et al. | | | |
| | | 5 | 5 | 1 | 4 | 6 | 9 | 6 | 5/7/96 | Murugesan et al. | | | |
| | | 5 | 5 | 7 | 1 | 8 | 2 | 1 | 11/5/96 | Chan et al. | | | |
| | | 5 | 5 | 1 | 4 | 6 | 9 | 1 | 5/7/96 | Chan et al. | | | |
| | | 5 | 5 | 9 | 1 | 7 | 6 | 1 | 1/7/97 | Chan et al. | | | |
| | | 5 | 5 | 9 | 4 | 0 | 2 | 1 | 1/14/97 | Chan et al. | | | |
| | | 5 | 6 | 1 | 2 | 3 | 5 | 9 | 3/18/97 | Murugesan | | | |

UNITED STATES PATENT AND TRADEMARK OFFICE
CERTIFICATE OF CORRRECTION

PATENT NO. : 5,846,985
DATED : Dec. 8, 1998
INVENTOR(S) : Natesan Murugesan Page 2 of 7

It is certified that error appears in the above-identified patent and that said Letters Patent is hereby corrected as shown below:

Title page, item [56] insert the following:
FOREIGN PATENT OR PUBLISHED FOREIGN PATENT APPLICATION

| | | | | DOCUMENT NUMBER | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 3 | 4 | 0 | 1 | 1/ | 9 | 3 | 9/9/93 | Australia | | | | |
| | | 6 | 7 | 3 | 5 | 7/ | 9 | 4 | 1/27/95 | Australia | | | | |
| | | 7 | 6 | 0 | 7 | 2 | | | 4/6/83 | Europe | | | | |
| | | 1 | 9 | 4 | 5 | 4 | 8 | | 9/17/86 | Europe | | | | |
| | | 4 | 4 | 3 | 9 | 8 | 3 | | 8/28/91 | Europe | | | | |
| | | 4 | 0 | 4 | 5 | 2 | 5 | | 12/27/90 | Europe | | | | |
| | | 5 | 2 | 6 | 7 | 0 | 8 | | 2/10/93 | Europe | | | | |
| | | 5 | 1 | 0 | 5 | 2 | 6 | | 10/28/92 | Europe | | | | |
| | | 5 | 6 | 9 | 1 | 9 | 3 | | 11/10/93 | Europe | | | | |
| | | 5 | 5 | 8 | 2 | 5 | 8 | | 9/1/93 | Europe | | | | |
| | | 6 | 2 | 6 | 1 | 7 | 4 | | 11/30/94 | Europe | | | | |
| | | 6 | 4 | 0 | 5 | 9 | 6 | | 3/1/95 | Europe | | | | |
| | | 6 | 3 | 4 | 1 | 7 | 5 | | 1/18/95 | Europe | | | | |
| | | 6 | 0 | 1 | 3 | 8 | 6 | | 6/15/94 | Europe | | | | |

UNITED STATES PATENT AND TRADEMARK OFFICE
CERTIFICATE OF CORRRECTION

PATENT NO. : 5,846,985
DATED : Dec. 8, 1998
INVENTOR(S) : Natesan Murugesan Page 3 of 7

It is certified that error appears in the above-identified patent and that said Letters Patent is hereby corrected as shown below:

Title page, item [56] insert the following:

FOREIGN PATENT OR PUBLISHED FOREIGN PATENT APPLICATION

|   |   | \multicolumn{6}{c}{DOCUMENT NUMBER} | PUBLICATION DATE | COUNTRY OR PATENT OFFICE | CLASS | SUBCLASS | TRANSLATION YES | NO |
|---|---|---|---|---|---|---|---|---|---|---|---|---|---|
|   |   | 6 | 1 | 7 | 0 | 0 | 1 |   | 9/28/94 | Europe |   |   |   |   |
|   |   | 6 | 3 | 3 | 2 | 5 | 9 |   | 1/11/95 | Europe |   |   |   |   |
|   |   | 1 | 0 | 5 | 9 | 4 | 5 | 9 | 6/59 | Germany |   |   |   |   |
|   |   | 0 | 8 | 9 | 7 | 4 | 4 | 0 | 5/62 | Great Britain |   |   |   |   |
|   |   | 2 | 2 | 2 | 8 | 9 | 3 | 3 | 9/12/90 | Great Britain |   |   |   |   |
|   |   | 8 | 0 | 4 | 0 | 3 | 6 |   | 11/58 | Great Britain |   |   |   |   |
|   |   | 1 | 4 | 7 | 3 | 4 | 3 | 3 | 5/11/77 | Great Britain |   |   |   |   |
|   |   | 0 | 3 | 6 | 4 | 5 | 0 | 6 | 11/62 | Switzerland |   |   |   |   |
|   |   | 9 | 3/ | 0 | 8 | 7 | 9 | 9 | 5/13/93 | World |   |   |   |   |
|   |   | 9 | 4/ | 2 | 7 | 9 | 7 | 9 | 12/8/94 | World |   |   |   |   |
|   |   | 9 | 3/ | 2 | 3 | 4 | 0 | 4 | 11/25/93 | World |   |   |   |   |
|   |   | 9 | 1/ | 1 | 5 | 4 | 7 | 9 | 10/17/91 | World |   |   |   |   |
|   |   | 9 | 3/ | 1 | 0 | 0 | 9 | 4 | 5/27/93 | World |   |   |   |   |
|   |   | 6 | 8 | 2 | 0 | 1 | 6 |   | 11/15/95 | Europe |   |   |   |   |

UNITED STATES PATENT AND TRADEMARK OFFICE
CERTIFICATE OF CORRRECTION

PATENT NO. : 5,846,985  
DATED : Dec. 8, 1998  
INVENTOR(S) : Natesan Murugesan Page 4 of 7

It is certified that error appears in the above-identified patent and that said Letters Patent is hereby corrected as shown below:

Title page, item [56] insert the following:

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 9 | 5/ | 2 | 6 | 9 | 5 | 7 | 10/12/95 | World | | | | |
| | | 4 | 8 | 0 | 3 | 9/ | 9 | 6 | 9/26/96 | Australia | | | | |
| | | 7 | 4 | 9 | 9 | 6 | 4 | | 12/27/96 | Europe | | | | |
| | | 9 | 6/ | 4 | 0 | 6 | 8 | 1 | 12/19/96 | World | | | | |
| | | 7 | 0 | 2 | 0 | 1 | 2 | | 3/20/96 | Europe | | | | |
| | | 9 | 6/ | 3 | 1 | 4 | 9 | 2 | 10/10/96 | World | | | | |
| | | 7 | 2 | 5 | 0 | 6 | 7 | | 8/7/96 | Europe | | | | |
| | | | | | | | | | | | | | | |

UNITED STATES PATENT AND TRADEMARK OFFICE
CERTIFICATE OF CORRRECTION

PATENT NO. : 5,846,985                                           Page 5 of 7
DATED : Dec. 8, 1998
INVENTOR(S) : Natesan Murugesan It is certified that error appears in the above-identified patent and that said Letters Patent is hereby corrected as shown below:

Title page, item [56] insert the following:

OTHER DOCUMENTS

| | |
|---|---|
| | S. Norio et al., Chemical Abstracts, Vol. 70, No. 19, (1969), 87639g. |
| | T. Saito, Chemical Abstracts, Vol. 73, No. 23 (1970), 120511w. |
| | Derwent Abstract No. 88-289069/41  2/27/87 |
| | Derwent Abstract No. 88-195835/28  11/26/86 |
| | Derwent Abstract No. 88-061295/09  7/9/86 |
| | Derwent Abstract No. 87-152485/22  10/11/85 |
| | Derwent Abstract No. 62299 E/30  12/11/80 |
| | Derwent Abstract No. 40927 D/23  9/11/79 |
| | Derwent Abstract No. 91-254550/35  2/19/90 |
| | Derwent Abstract No. 86-246709/38  11/27/85 |
| | Derwent Abstract No. 35012 K/15  9/24/81 |
| | Allen et al., "Preparation...antagonists", CA116(11):106284Z, p. 778, 1992 |
| | R.D. Desai et al., Chemical Abstracts, Vol. 71, No. 11, (1969) 49825c |
| | R.D. Desai et al., Chemical Abstracts, Vol. 71, No. 3, (1969) 12872q |

UNITED STATES PATENT AND TRADEMARK OFFICE
CERTIFICATE OF CORRRECTION

PATENT NO. : 5,846,985
DATED : Dec. 8, 1998
INVENTOR(S) : Natesan Murugesan It is certified that error appears in the above-identified patent and that said Letters Patent is hereby corrected as shown below:

Title page, item [56] insert the following:

OTHER DOCUMENTS

|   |   | |
|---|---|---|
| | | P. G. Ferrini et al., Angew. Chem. Internat. Edit., Vol. 2, No. 2 (1963) p. 99 |
| | | A.M. van Leusen, et al., "Synthesis...Compounds", J. Org. Chem., Vol. 41, No. 4, (1976), pp. 69-71 |
| | | W. J. Hammar et al., J Heterocyclic Chem., Vol. 18, (1981) pp. 885-888 |
| | | A. M. van Leusen, et al., Tetrahedron Letters, No. 23, (1972), pp. 2369-2372. |
| | | Chan et al., "Identification of a New Class of ETA Selective Endothelin Antagonists by Pharmacophore Directed Screening", Biochemical and Biophysical Research Communications, Vol. 201, No. 1, May 30, 1994, pp. 228-234 |
| | | Stein et al., "The Discovery of Sulfonamide Endothelin Antagonists and the Development of the Orally Active ETA Antagonist 5-(Dimethylamino)-N-(3,4-dimethyl-5-isoxazolyl)-1-naphthalenesulfonamide", J. Med. Chem., Vol. 37, No. 3, February 4, 1994, pp. 329-331 |
| | | Doherty, J. Med. Chem., 35(9), 1493-1508 (May 1992) |
| | | CA 65: 2241d (1966) |
| | | CA 92: 41908v (1979) |

UNITED STATES PATENT AND TRADEMARK OFFICE
CERTIFICATE OF CORRRECTION

PATENT NO. : 5,846,985
DATED : Dec. 8, 1998
INVENTOR(S) : Natesan Murugesan It is certified that error appears in the above-identified patent and that said Letters Patent is hereby corrected as shown below:

Title page, item [56] insert the following:

OTHER DOCUMENTS

|  |  |  |
|--|--|--|
|  | | Wang et al., "Nitrile...sinomin," CA 108:94444w, p. 651 (1988) |
|  | | Khanna, "Oral...formulation," CA 115:35728p, p. 415 (1991) |
|  | | Stein et al., "The Discovery...1-naphthalenesulfonamide," CA 120: 18233n, p. 21-22 (1994) |
|  | | Vree et al., "Renal excretion...function," CA 97:84685r, p.23 (1982) |
|  | | Oie, "Pharmacokinetics...dosing," CA 102:197512x, p. 18 (1985) |
|  | | Murugesan et al., "N-(heteroaryl)...antagonists," CA 120:270370c, p. 1067 (1994) |

Signed and Sealed this

Thirteenth Day of April, 1999

Attest:

Q. TODD DICKINSON

*Attesting Officer*    *Acting Commissioner of Patents and Trademarks*

UNITED STATES PATENT AND TRADEMARK OFFICE
CERTIFICATE OF CORRRECTION

PATENT NO. : 5,846,985
DATED : Dec.8, 1998
INVENTOR(S) : Natesan Mjrugesan

Page 1 of 7

It is certified that error appears in the above-identified patent and that said Letters Patent is hereby corrected as shown below:

On the title page, item [56], insert the following:

U. S. PATENT DOCUMENTS

| EXAMINER INITIAL | | PATENT NUMBER | | | | | | | ISSUE DATE | PATENTEE | CLASS | SUBCLASS | FILING DATE IF APPROPRIATE |
|---|---|---|---|---|---|---|---|---|---|---|---|---|---|
| | | 2 | 8 | 8 | 8 | 4 | 5 | 5 | 5/26/59 | Kano et al. | | | |
| | | 4 | 4 | 1 | 5 | 4 | 9 | 6 | 11/15/83 | Harris et al. | | | |
| | | 4 | 6 | 6 | 1 | 4 | 7 | 9 | 4/87 | Wyvratt, Jr. et al. | | | |
| | | 5 | 2 | 3 | 6 | 9 | 2 | 8 | 8/17/93 | Chakravarty et al. | | | |
| | | 5 | 2 | 7 | 0 | 3 | 1 | 3 | 12/14/93 | Burri et al. | | | |
| | | 5 | 2 | 9 | 2 | 7 | 4 | 0 | 3/8/94 | Burri et al. | | | |
| | | 5 | 3 | 7 | 8 | 7 | 1 | 5 | 1/3/95 | Stein et al. | | | |
| | | 5 | 4 | 6 | 4 | 8 | 5 | 3 | 11/7/95 | Chan et al. | | | |
| | | 5 | 5 | 1 | 4 | 6 | 9 | 6 | 5/7/96 | Murugesan et al. | | | |
| | | 5 | 5 | 7 | 1 | 8 | 2 | 1 | 11/5/96 | Chan et al. | | | |
| | | 5 | 5 | 1 | 4 | 6 | 9 | 1 | 5/7/96 | Chan et al. | | | |
| | | 5 | 5 | 9 | 1 | 7 | 6 | 1 | 1/7/97 | Chan et al. | | | |
| | | 5 | 5 | 9 | 4 | 0 | 2 | 1 | 1/14/97 | Chan et al. | | | |
| | | 5 | 6 | 1 | 2 | 3 | 5 | 9 | 3/18/97 | Murugesan | | | |

UNITED STATES PATENT AND TRADEMARK OFFICE
CERTIFICATE OF CORRRECTION

PATENT NO. : 5,846,985
DATED : Dec.8, 1998
INVENTOR(S) : Natesan Mjrugesan

Page 2 of 7

It is certified that error appears in the above-identified patent and that said Letters Patent is hereby corrected as shown below:

FOREIGN PATENT OR PUBLISHED FOREIGN PATENT APPLICATION

| | | | | DOCUMENT NUMBER | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 3 | 4 | 0 | 1 | 1/ | 9 | 3 | 9/9/93 | Australia | | | | |
| | | 6 | 7 | 3 | 5 | 7/ | 9 | 4 | 1/27/95 | Australia | | | | |
| | | 7 | 6 | 0 | 7 | 2 | | | 4/6/83 | Europe | | | | |
| | | 1 | 9 | 4 | 5 | 4 | 8 | | 9/17/86 | Europe | | | | |
| | | 4 | 4 | 3 | 9 | 8 | 3 | | 8/28/91 | Europe | | | | |
| | | 4 | 0 | 4 | 5 | 2 | 5 | | 12/27/90 | Europe | | | | |
| | | 5 | 2 | 6 | 7 | 0 | 8 | | 2/10/93 | Europe | | | | |
| | | 5 | 1 | 0 | 5 | 2 | 6 | | 10/28/92 | Europe | | | | |
| | | 5 | 6 | 9 | 1 | 9 | 3 | | 11/10/93 | Europe | | | | |
| | | 5 | 5 | 8 | 2 | 5 | 8 | | 9/1/93 | Europe | | | | |
| | | 6 | 2 | 6 | 1 | 7 | 4 | | 11/30/94 | Europe | | | | |
| | | 6 | 4 | 0 | 5 | 9 | 6 | | 3/1/95 | Europe | | | | |
| | | 6 | 3 | 4 | 1 | 7 | 5 | | 1/18/95 | Europe | | | | |
| | | 6 | 0 | 1 | 3 | 8 | 6 | | 6/15/94 | Europe | | | | |

UNITED STATES PATENT AND TRADEMARK OFFICE
CERTIFICATE OF CORRRECTION

PATENT NO. : 5,846,985  
DATED : Dec.8, 1998  
INVENTOR(S) : Natesan Mjrugesan Page 3 of 7

It is certified that error appears in the above-identified patent and that said Letters Patent is hereby corrected as shown below:

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 6 | 1 | 7 | 0 | 0 | 1 | 9/28/94 | Europe | | | | |
| | | 6 | 3 | 3 | 2 | 5 | 9 | 1/11/95 | Europe | | | | |
| | | 1 | 0 | 5 | 9 | 4 | 5 | 9 | 6/59 | Germany | | | |
| | | 0 | 8 | 9 | 7 | 4 | 4 | 0 | 5/62 | Great Britain | | | |
| | | 2 | 2 | 8 | 9 | 3 | 3 | 9/12/90 | Great Britain | | | | |
| | | 8 | 0 | 4 | 0 | 3 | 6 | 11/58 | Great Britain | | | | |
| | | 1 | 4 | 7 | 3 | 4 | 3 | 3 | 5/11/77 | Great Britain | | | |
| | | 0 | 3 | 6 | 4 | 5 | 0 | 6 | 11/62 | Switzerland | | | |
| | | 9 | 3/ | 0 | 8 | 7 | 9 | 9 | 5/13/93 | World | | | |
| | | 9 | 4/ | 2 | 7 | 9 | 7 | 9 | 12/8/94 | World | | | |
| | | 9 | 3/ | 2 | 3 | 4 | 0 | 4 | 11/25/93 | World | | | |
| | | 9 | 1/ | 1 | 5 | 4 | 7 | 9 | 10/17/91 | World | | | |
| | | 9 | 3/ | 1 | 0 | 0 | 9 | 4 | 5/27/93 | World | | | |
| | | 6 | 8 | 2 | 0 | 1 | 6 | 11/15/95 | Europe | | | | |

UNITED STATES PATENT AND TRADEMARK OFFICE
CERTIFICATE OF CORRRECTION

PATENT NO. : 5,846,985
DATED : Dec.8, 1998
INVENTOR(S) : Natesan Mjrugesan

It is certified that error appears in the above-identified patent and that said Letters Patent is hereby corrected as shown below:

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 9 | 5/ | 2 | 6 | 9 | 5 | 7 | 10/12/95 | World | | | | |
| | | 4 | 8 | 0 | 3 | 9/ | 9 | 6 | 9/26/96 | Australia | | | | |
| | | 7 | 4 | 9 | 9 | 6 | 4 | | 12/27/96 | Europe | | | | |
| | | 9 | 6/ | 4 | 0 | 6 | 8 | 1 | 12/19/96 | World | | | | |
| | | 7 | 0 | 2 | 0 | 1 | 2 | | 3/20/96 | Europe | | | | |
| | | 9 | 6/ | 3 | 1 | 4 | 9 | 2 | 10/10/96 | World | | | | |
| | | 7 | 2 | 5 | 0 | 6 | 7 | | 8/7/96 | Europe | | | | |
| | | | | | | | | | | | | | | |

UNITED STATES PATENT AND TRADEMARK OFFICE
CERTIFICATE OF CORRRECTION

PATENT NO. : 5,846,985  
DATED : Dec.8, 1998  
INVENTOR(S) : Natesan Mjrugesan Page 5 of 7

It is certified that error appears in the above-identified patent and that said Letters Patent is hereby corrected as shown below:

OTHER DOCUMENTS

| | |
|---|---|
| | S. Norio et al., Chemical Abstracts, Vol. 70, No. 19, (1969), 87639g. |
| | T. Saito, Chemical Abstracts, Vol. 73, No. 23 (1970), 120511w. |
| | Derwent Abstract No. 88-289069/41  2/27/87 |
| | Derwent Abstract No. 88-195835/28  11/26/86 |
| | Derwent Abstract No. 88-061295/09  7/9/86 |
| | Derwent Abstract No. 87-152485/22  10/11/85 |
| | Derwent Abstract No. 62299 E/30  12/11/80 |
| | Derwent Abstract No. 40927 D/23  9/11/79 |
| | Derwent Abstract No. 91-254550/35  2/19/90 |
| | Derwent Abstract No. 86-246709/38  11/27/85 |
| | Derwent Abstract No. 35012 K/15  9/24/81 |
| | Allen et al., "Preparation...antagonists", CA116(11):106284Z, p. 778, 1992 |
| | R.D. Desai et al., Chemical Abstracts, Vol. 71, No. 11, (1969) 49825c |
| | R.D. Desai et al., Chemical Abstracts, Vol. 71, No. 3, (1969) 12872q |

UNITED STATES PATENT AND TRADEMARK OFFICE
CERTIFICATE OF CORRRECTION

PATENT NO. : 5,846,985
DATED : Dec.8, 1998
INVENTOR(S) : Natesan Mjrugesan It is certified that error appears in the above-identified patent and that said Letters Patent is hereby corrected as shown below:

OTHER DOCUMENTS

| | |
|---|---|
| | P. G. Ferrini et al., Angew. Chem. Internat. Edit., Vol. 2, No. 2 (1963) p. 99 |
| | A.M. van Leusen, et al., "Synthesis...Compounds", J. Org. Chem., Vol. 41, No. 4, (1976), pp. 69-71 |
| | W. J. Hammar et al., J Heterocyclic Chem., Vol. 18, (1981) pp. 885-888 |
| | A. M. van Leusen, et al., Tetrahedron Letters, No. 23, (1972), pp. 2369-2372. |
| | Chan et al., "Identification of a New Class of ETA Selective Endothelin Antagonists by Pharmacophore Directed Screening", Biochemical and Biophysical Research Communications, Vol. 201, No. 1, May 30, 1994, pp. 228-234 |
| | Stein et al., "The Discovery of Sulfonamide Endothelin Antagonists and the Development of the Orally Active ETA Antagonist 5-(Dimethylamino)-N-(3,4-dimethyl-5-isoxazolyl)-1-naphthalenesulfonamide", J. Med. Chem., Vol. 37, No. 3, February 4, 1994, pp. 329-331 |
| | Doherty, J. Med. Chem., 35(9), 1493-1508 (May 1992) |
| | CA 65: 2241d (1966) |
| | CA 92: 41908v (1979) |

UNITED STATES PATENT AND TRADEMARK OFFICE
CERTIFICATE OF CORRRECTION

PATENT NO. : 5,846,985
DATED : Dec.8, 1998
INVENTOR(S) : Natesan Mjrugesan Page 7 of 7

It is certified that error appears in the above-identified patent and that said Letters Patent is hereby corrected as shown below:

OTHER DOCUMENTS

| | | |
|---|---|---|
| | | Wang et al., "Nitrile...sinomin," CA 108:94444w, p. 651 (1988) |
| | | Khanna, "Oral...formulation," CA 115:35728p, p. 415 (1991) |
| | | Stein et al., "The Discovery...1-naphthalenesulfonamide," CA 120: 18233n, p. 21-22 (1994) |
| | | Vree et al., "Renal excretion...function," CA 97:84685r, p.23 (1982) |
| | | Oie, "Pharmacokinetics...dosing," CA 102:197512x, p. 18 (1985) |
| | | Murugesan et al., "N-(heteroaryl)...antagonists," CA 120:270370c, p. 1067 (1994) |

Signed and Sealed this

First Day of June, 1999

Attest:

Q. TODD DICKINSON

*Attesting Officer*   *Acting Commissioner of Patents and Trademarks*

UNITED STATES PATENT AND TRADEMARK OFFICE
CERTIFICATE OF CORRRECTION

PATENT NO. : 5,846,985　　　　　　　　　　　　　　　Page 1 of 7
DATED : December 8, 1998
INVENTOR(S) :
Natesan Murugesan It is certified that error appears in the above-identified patent and that said Letters Patent is hereby corrected as shown below:

On the title page, item [56], insert the following:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 2 | 8 | 8 | 8 | 4 | 5 | 5/26/59 | Kano et al. | | | |
| | | 4 | 4 | 1 | 5 | 4 | 9 | 11/15/83 | Harris et al. | | | |
| | | 4 | 6 | 6 | 1 | 4 | 7 | 4/87 | Wyvratt, Jr. et al. | | | |
| | | 5 | 2 | 3 | 6 | 9 | 2 | 8/17/93 | Chakravarty et al. | | | |
| | | 5 | 2 | 7 | 0 | 3 | 1 | 12/14/93 | Burri et al. | | | |
| | | 5 | 2 | 9 | 2 | 7 | 4 | 3/8/94 | Burri et al. | | | |
| | | 5 | 3 | 7 | 8 | 7 | 1 | 1/3/95 | Stein et al. | | | |
| | | 5 | 4 | 6 | 4 | 8 | 5 | 11/7/95 | Chan et al. | | | |
| | | 5 | 5 | 1 | 4 | 6 | 9 | 5/7/96 | Murugesan et al. | | | |
| | | 5 | 5 | 7 | 1 | 8 | 2 | 11/5/96 | Chan et al. | | | |
| | | 5 | 5 | 1 | 4 | 6 | 9 | 5/7/96 | Chan et al. | | | |
| | | 5 | 5 | 9 | 1 | 7 | 6 | 1/7/97 | Chan et al. | | | |
| | | 5 | 5 | 9 | 4 | 0 | 2 | 1/14/97 | Chan et al. | | | |
| | | 5 | 6 | 1 | 2 | 3 | 5 | 3/18/97 | Murugesan | | | |

UNITED STATES PATENT AND TRADEMARK OFFICE
CERTIFICATE OF CORRRECTION

PATENT NO. : 5,846,985

DATED : December 8, 1998

INVENTOR(S) : Natesan Murugesan

It is certified that error appears in the above-identified patent and that said Letters Patent is hereby corrected as shown below:

Title page, item [56], insert the following;

FOREIGN PATENT OR PUBLISHED FOREIGN PATENT APPLICATION

| | | \multicolumn{7}{c|}{DOCUMENT NUMBER} | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 3 | 4 | 0 | 1 | 1/ | 9 | 3 | 9/9/93 | Australia | | | | |
| | | 6 | 7 | 3 | 5 | 7/ | 9 | 4 | 1/27/95 | Australia | | | | |
| | | 7 | 6 | 0 | 7 | 2 | | | 4/6/83 | Europe | | | | |
| | | 1 | 9 | 4 | 5 | 4 | 8 | | 9/17/86 | Europe | | | | |
| | | 4 | 4 | 3 | 9 | 8 | 3 | | 8/28/91 | Europe | | | | |
| | | 4 | 0 | 4 | 5 | 2 | 5 | | 12/27/90 | Europe | | | | |
| | | 5 | 2 | 6 | 7 | 0 | 8 | | 2/10/93 | Europe | | | | |
| | | 5 | 1 | 0 | 5 | 2 | 6 | | 10/28/92 | Europe | | | | |
| | | 5 | 6 | 9 | 1 | 9 | 3 | | 11/10/93 | Europe | | | | |
| | | 5 | 5 | 8 | 2 | 5 | 8 | | 9/1/93 | Europe | | | | |
| | | 6 | 2 | 6 | 1 | 7 | 4 | | 11/30/94 | Europe | | | | |
| | | 6 | 4 | 0 | 5 | 9 | 6 | | 3/1/95 | Europe | | | | |
| | | 6 | 3 | 4 | 1 | 7 | 5 | | 1/18/95 | Europe | | | | |
| | | 6 | 0 | 1 | 3 | 8 | 6 | | 6/15/94 | Europe | | | | |

UNITED STATES PATENT AND TRADEMARK OFFICE
CERTIFICATE OF CORRRECTION

PATENT NO. : 5,846,985                             Page 3 of 7
DATED : December 8, 1998
INVENTOR(S) : Natesan Murugesan It is certified that error appears in the above-identified patent and that said Letters Patent is hereby corrected as shown below:

Title page, item [56], insert the following;

FOREIGN PATENT OR PUBLISHED FOREIGN PATENT APPLICATION

| | | | | DOCUMENT NUMBER | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 6 | 1 | 7 | 0 | 0 | 1 | 9/28/94 | Europe | | | | |
| | | 6 | 3 | 3 | 2 | 5 | 9 | 1/11/95 | Europe | | | | |
| | | 1 | 0 | 5 | 9 | 4 | 5 | 9 | 6/59 | Germany | | | |
| | | 0 | 8 | 9 | 7 | 4 | 4 | 0 | 5/62 | Great Britain | | | |
| | | 2 | 2 | 2 | 8 | 9 | 3 | 3 | 9/12/90 | Great Britain | | | |
| | | 8 | 0 | 4 | 0 | 3 | 6 | 11/58 | Great Britain | | | | |
| | | 1 | 4 | 7 | 3 | 4 | 3 | 3 | 5/11/77 | Great Britain | | | |
| | | 0 | 3 | 6 | 4 | 5 | 0 | 6 | 11/62 | Switzerland | | | |
| | | 9 | 3/ | 0 | 8 | 7 | 9 | 9 | 5/13/93 | World | | | |
| | | 9 | 4/ | 2 | 7 | 9 | 7 | 9 | 12/8/94 | World | | | |
| | | 9 | 3/ | 2 | 3 | 4 | 0 | 4 | 11/25/93 | World | | | |
| | | 9 | 1/ | 1 | 5 | 4 | 7 | 9 | 10/17/91 | World | | | |
| | | 9 | 3/ | 1 | 0 | 0 | 9 | 4 | 5/27/93 | World | | | |
| | | 6 | 8 | 2 | 0 | 1 | 6 | 11/15/95 | Europe | | | | |

UNITED STATES PATENT AND TRADEMARK OFFICE
CERTIFICATE OF CORRRECTION

PATENT NO. : 5,846,985
DATED : December 8, 1998
INVENTOR(S) : Natesan Murugesan It is certified that error appears in the above-identified patent and that said Letters Patent is hereby corrected as shown below:

Title page, item [56], insert the following;

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 9 | 5 | 2 | 6 | 9 | 5 | 7 | 10/12/95 | World | | | | |
| | | 4 | 8 | 0 | 3 | 9 | 9 | 6 | 9/26/96 | Australia | | | | |
| | | 7 | 4 | 9 | 9 | 6 | 4 | | 12/27/96 | Europe | | | | |
| | | 9 | 6 | 4 | 0 | 6 | 8 | 1 | 12/19/96 | World | | | | |
| | | 7 | 0 | 2 | 0 | 1 | 2 | | 3/20/96 | Europe | | | | |
| | | 9 | 6 | 3 | 1 | 4 | 9 | 2 | 10/10/96 | World | | | | |
| | | 7 | 2 | 5 | 0 | 6 | 7 | | 8/7/96 | Europe | | | | |
| | | | | | | | | | | | | | | |

UNITED STATES PATENT AND TRADEMARK OFFICE
CERTIFICATE OF CORRRECTION

PATENT NO. : 5,846,985      Page 5 of 7
DATED : December 8, 1998
INVENTOR(S) : Natesan Murugesan It is certified that error appears in the above-identified patent and that said Letters Patent is hereby corrected as shown below:

Title page, item [56], insert the following:

OTHER DOCUMENTS

| | | |
|---|---|---|
| | | S. Norio et al., Chemical Abstracts, Vol. 70, No. 19, (1969), 87639g. |
| | | T. Saito, Chemical Abstracts, Vol. 73, No. 23 (1970), 120511w. |
| | | Derwent Abstract No. 88-289069/41  2/27/87 |
| | | Derwent Abstract No. 88-195835/28  11/26/86 |
| | | Derwent Abstract No. 88-061295/09  7/9/86 |
| | | Derwent Abstract No. 87-152485/22  10/11/85 |
| | | Derwent Abstract No. 62299 E/30  12/11/80 |
| | | Derwent Abstract No. 40927 D/23  9/11/79 |
| | | Derwent Abstract No. 91-254550/35  2/19/90 |
| | | Derwent Abstract No. 86-246709/38  11/27/85 |
| | | Derwent Abstract No. 35012 K/15  9/24/81 |
| | | Allen et al., "Preparation...antagonists", CA116(11):106284Z, p. 778, 1992 |
| | | R.D. Desai et al., Chemical Abstracts, Vol. 71, No. 11, (1969) 49825c |
| | | R.D. Desai et al., Chemical Abstracts, Vol. 71, No. 3, (1969) 12872q |

UNITED STATES PATENT AND TRADEMARK OFFICE
CERTIFICATE OF CORRRECTION

PATENT NO. : 5,846,985
DATED : December 8, 1998
INVENTOR(S) : Natesan Murugesan It is certified that error appears in the above-identified patent and that said Letters Patent is hereby corrected as shown below:

On the title page, item [56], insert the following:

OTHER DOCUMENTS

|   |   |   |
|---|---|---|
|   |   | P. G. Ferrini et al., Angew. Chem. Internat. Edit., Vol. 2, No. 2 (1963) p. 99 |
|   |   | A.M. van Leusen, et al., "Synthesis...Compounds", J. Org. Chem., Vol. 41, No. 4, (1976), pp. 69-71 |
|   |   | W. J. Hammar et al., J Heterocyclic Chem., Vol. 18, (1981) pp. 885-888 |
|   |   | A. M. van Leusen, et al., Tetrahedron Letters, No. 23, (1972), pp. 2369-2372. |
|   |   | Chan et al., "Identification of a New Class of ETA Selective Endothelin Antagonists by Pharmacophore Directed Screening", Biochemical and Biophysical Research Communications, Vol. 201, No. 1, May 30, 1994, pp. 228-234 |
|   |   | Stein et al., "The Discovery of Sulfonamide Endothelin Antagonists and the Development of the Orally Active ETA Antagonist 5-(Dimethylamino)-N-(3,4-dimethyl-5-isoxazolyl)-1-naphthalenesulfonamide", J. Med. Chem., Vol. 37, No. 3, February 4, 1994, pp. 329-331 |
|   |   | Doherty, J. Med. Chem., 35(9), 1493-1508 (May 1992) |
|   |   | CA 65: 2241d (1966) |
|   |   | CA 92: 41908v (1979) |

UNITED STATES PATENT AND TRADEMARK OFFICE
CERTIFICATE OF CORRRECTION

PATENT NO. : 5,846,985
DATED : December 8, 1998
INVENTOR(S) : Natesan Murugesan It is certified that error appears in the above-identified patent and that said Letters Patent is hereby corrected as shown below:

On the title page, item [56], insert the following:

OTHER DOCUMENTS

| | | |
|--|--|--|
| | | Wang et al., "Nitrile...sinomin," CA 108:94444w, p. 651 (1988) |
| | | Khanna, "Oral...formulation," CA 115:35728p, p. 415 (1991) |
| | | Stein et al., "The Discovery...1-naphthalenesulfonamide," CA 120: 18233n, p. 21-22 (1994) |
| | | Vree et al., "Renal excretion...function," CA 97:84685r, p.23 (1982) |
| | | Oie, "Pharmacokinetics...dosing," CA 102:197512x, p. 18 (1985) |
| | | Murugesan et al., "N-(heteroaryl)...antagonists," CA 120:270370c, p. 1067 (1994) |

Signed and Sealed this

Nineteenth Day of October, 1999

Attest:

Q. TODD DICKINSON

*Attesting Officer*

*Acting Commissioner of Patents and Trademarks*

UNITED STATES PATENT AND TRADEMARK OFFICE
CERTIFICATE OF CORRECTION

PATENT NO. : 5,846,985  Page 1 of 1
DATED : December 8, 1998
INVENTOR(S) : Natesan Murugesan It is certified that error appears in the above-identified patent and that said Letters Patent is hereby corrected as shown below:

Column 18,
Line 36, should read -- p is 0 or an integer from 1 to 2, with the proviso that, when K is C=O, J is N and the heterocycle containing Q, K and J is bonded through J, p is not 1. --

Signed and Sealed this

Eighth Day of October, 2002

*Attest:*

*Attesting Officer*

JAMES E. ROGAN
*Director of the United States Patent and Trademark Office*